(12) United States Patent
Eide (10) Patent No.: US 9,623,374 B2
(45) Date of Patent: Apr. 18, 2017

(54) ACTIVE PHOTOCATALYTIC OXIDATION

(75) Inventor: Andrew Eide, Rockwall, TX (US)

(73) Assignee: DBG GROUP INVESTMENTS LLC, Dallas, TX (US)

( * ) Notice: Subject to any disclaimer, the term of this patent is extended or adjusted under 35 U.S.C. 154(b) by 13 days.

(21) Appl. No.: 13/602,102

(22) Filed: Sep. 1, 2012

(65) Prior Publication Data

US 2014/0065023 A1    Mar. 6, 2014

(51) Int. Cl.
*A61L 9/20*   (2006.01)
*B01D 53/88*  (2006.01)
*A61L 2/08*   (2006.01)

(52) U.S. Cl.
CPC ............ *B01D 53/885* (2013.01); *A61L 2/088* (2013.01); *A61L 9/205* (2013.01); *B01D 2255/802* (2013.01); *B01D 2258/06* (2013.01); *B01D 2259/804* (2013.01)

(58) Field of Classification Search
CPC ... A61L 2/00; A61L 2/08; A61L 2/088; A61L 9/00; A61L 9/16; A61L 9/18; A61L 9/20; A61L 9/205; A61L 2202/00; A61L 2202/10; A61L 2202/11; A61L 2209/00; A61L 2209/10; A61L 2209/20; A61L 2/10; A61L 2209/212; B01J 35/00; B01J 35/002; B01J 35/004; B01J 35/04; B01D 53/885; B01D 2259/804; B01D 2258/06; B01D 2255/802
USPC ........ 422/186.3, 22, 24, 120–122, 168, 177, 422/180
See application file for complete search history.

(56) References Cited

U.S. PATENT DOCUMENTS

| | | | |
|---|---|---|---|
| 6,238,631 B1 | 5/2001 | Ogata et al. | |
| 7,425,226 B2 | 9/2008 | Powell | |
| 7,674,436 B1 * | 3/2010 | Feldman et al. | ............... 422/121 |
| 8,658,101 B1 | 2/2014 | Burnett | |
| 9,011,780 B1 | 4/2015 | Burnett | |
| 2006/0057020 A1 * | 3/2006 | Tufo | ............... 422/24 |
| 2006/0262389 A1 | 11/2006 | Zaczek | |
| 2009/0035176 A1 * | 2/2009 | Normark et al. | ................. 422/4 |
| 2009/0041617 A1 | 2/2009 | Lee | |
| 2012/0000860 A1 | 1/2012 | Arenshtam et al. | |
| 2012/0315184 A1 | 12/2012 | Clark | |
| 2014/0065023 A1 | 3/2014 | Eide | |
| 2014/0091230 A1 | 4/2014 | Clark et al. | |

OTHER PUBLICATIONS

PCT: International Search Report and Written Opinion of PCT/US15/33364 (related application); Sep. 4, 2015; 16 pgs.

* cited by examiner

*Primary Examiner* — Timothy Cleveland
(74) *Attorney, Agent, or Firm* — Howison & Arnott, LLP (57) ABSTRACT

Embodiments of the present disclosure could generally provide an active oxidation and purifying system to maximize the rate of photocatalytic oxidation and ambient air filtration by structurally optimizing the system to maximize potential ultraviolet (UV) light exposure to the surface and apertures of the active power cells. In one example, the active power cells could include a plurality of apertures disposed in a transverse manner from the first surface to the second surface of the active power cell. For example, the first set of the apertures could be disposed about 45 degrees relative to a median axis along the first and second surfaces, while a second set of apertures could be disposed about negative 45 degrees relative to the same median axis.

9 Claims, 8 Drawing Sheets

ACTIVE PHOTOCATALYTIC OXIDATION

The present disclosure relates generally to air filtering or purifying systems and, in particular, to systems and methods of using ultraviolet light to oxidize and purify the ambient environment using photocatalytic oxidation.

BACKGROUND

Conventional systems, such as high-efficiency particulate air (HEPA) filtration systems, require contaminates to come in direct contact with a filter to remove such contaminants and fail to address any surface contaminants. Other conventional systems using ultraviolet light to oxidize ambient air typically use particle filters that, when energized by a centrally located ultraviolet (UV) light source, aid in purifying the ambient air and environment by converting toxic compounds to benign constituents. Such systems typically include rows of coated particle filters that form a structure to selectively envelope the UV light source. The UV light in such systems fail to adequately expose the surfaces of conventional particle filters and, thus, such systems typically yield rates of photocatalytic oxidation and air filtration that are relatively low.

What is needed, however, is an effective and efficient system of increasing the rate of photocatalytic oxidation to ultimately increase the rate and efficiency of oxidizing and purifying the ambient environment.

SUMMARY

Embodiments of the present disclosure generally provide systems and methods of using ultraviolet light and photocatalytic oxidation to oxidize and purify the ambient environment.

In one embodiment, the present disclosure could provide a photocatalytic oxidation system. The system could include an active power cell having a first surface and a second surface. The system could also include a plurality of apertures disposed in a transverse manner from the first surface to the second surface.

In another embodiment, the present disclosure could provide an active photocatalytic oxidation system having an ultraviolet (UV) light source. The system could include an active power cell having a first surface exposed to the ambient environment and a second surface exposed to the UV light source. The active power cell could include a plurality of apertures disposed in a transverse manner from the first surface to the second surface.

In still another embodiment, the present disclosure could include an active photocatalytic oxidation system having an ultraviolet (UV) light source and an active power cell comprising a material capable of photocatalytic oxidation. The active power cell could include a first surface exposed to the ambient environment and a second surface exposed to the UV light source. The active power cell could include a plurality of apertures disposed in a transverse manner from the first surface to the second surface.

Other technical features may be readily apparent to one skilled in the art from the following figures and descriptions.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

The present disclosure relates generally to air purifications systems and methods, in particular, to systems and methods of using ultraviolet light and photocatalytic oxidation to oxidize and purify the ambient environment.

In one embodiment, the present disclosure could include an active power cell having multiple rows of selectively arranged specially treated and coated cell apertures that, when energized by a centrally located ultraviolet (UV) light source, aid in oxidizing and purifying the ambient air, surrounding surfaces, or ambient environment by converting toxic compounds to benign constituents and controlling or neutralizing contaminants in the ambient environment. The multiple rows of cell apertures could form a honeycomb-like or other suitable structure selectively positioned to envelope the UV light source. By selectively positioning the cell apertures to maximize UV exposure, the active power cell increases the relative rates of photocatalytic oxidation and purification when compared to conventional oxidation systems, purification systems, or particle filters.

Figure 1A:
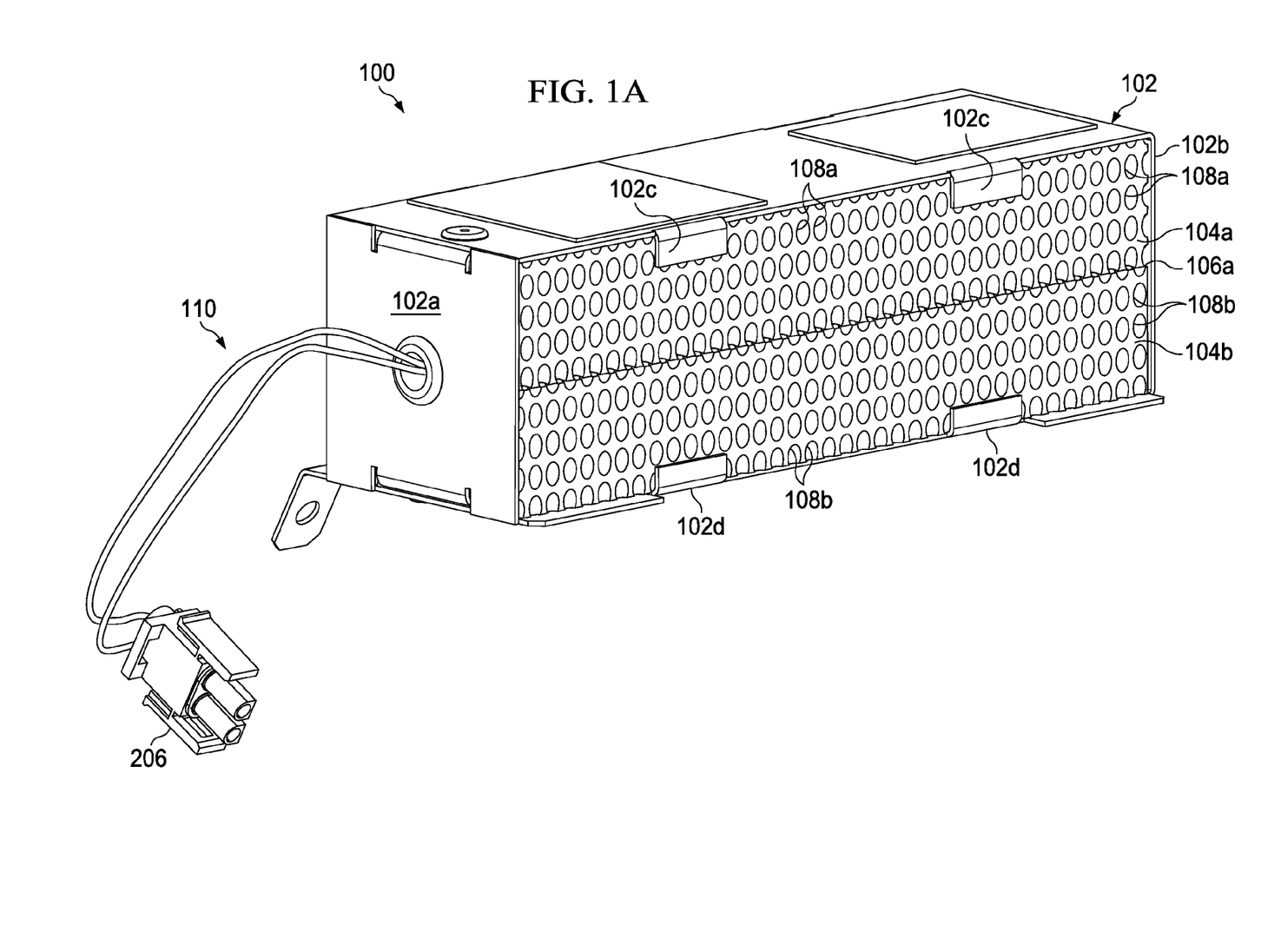
FIGS. 1A and 1B are somewhat simplified perspective views of an active photocatalytic oxidation system having an active power cell in accordance with one embodiment of the present disclosure.
Figure 1B:
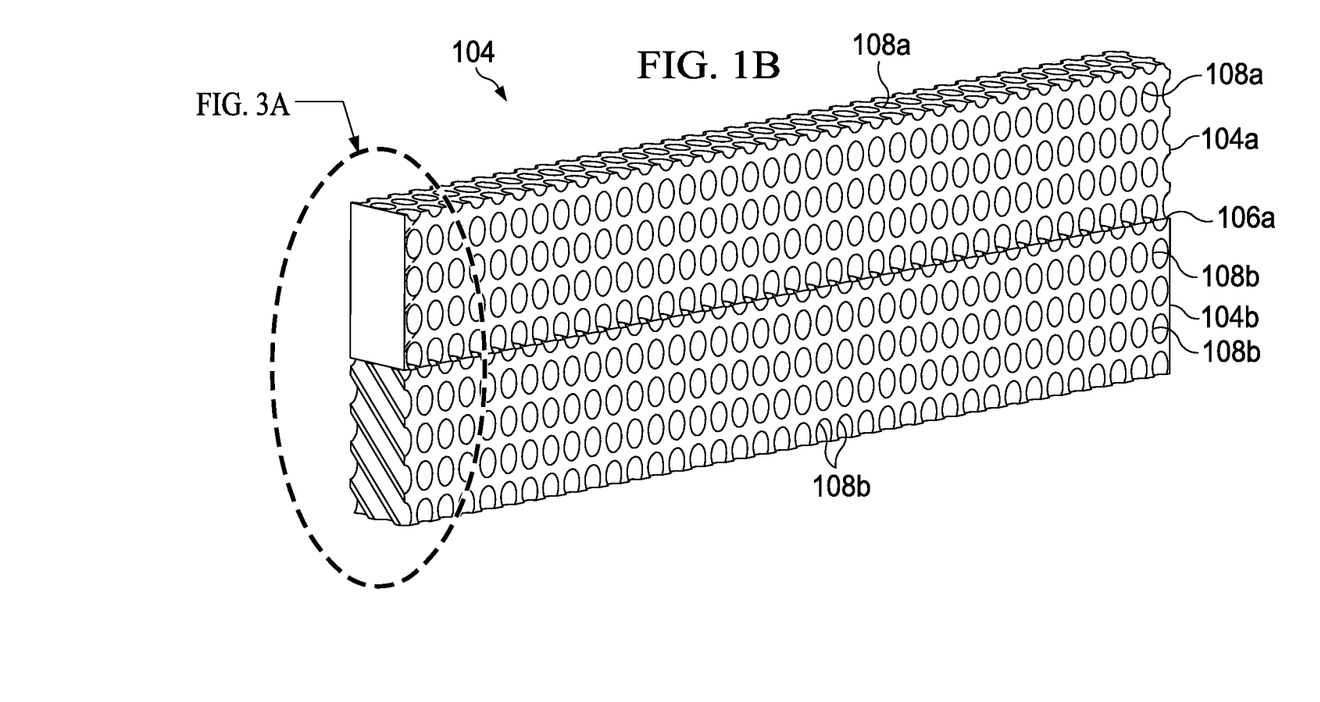

FIGS. 1A and 1B are somewhat simplified perspective views of system 100 in accordance with one embodiment of the present disclosure. In one embodiment, system 100 could include housing 102, active power cells 104, medians 106, cell apertures 108, and lighting assembly 110 as generally shown in FIGS. 1A and 1B and described in further detail herein. It should be understood that system 100 and active power cell 104 could include, for example, any suitable purification system, oxidation system, particle filtering system, active power cell system, photocatalytic system, neutralizing systems, air filtration system, or combination thereof. It should also be understood that system 100 and active power cell 104 shown in FIGS. 1A and 1B are for illustrative purposes only and that any other suitable system or subsystem could be used in conjunction with or in lieu of system 100 or active power cell 104 according to one embodiment of the present disclosure.

Housing 102 could include any suitably sized, shaped or configured frame, frame-like structure, housing, or housing-like structure to aid in maintaining a particular configuration of two or more active power cells 104 relative to each other according to one embodiment of the present disclosure. In one embodiment, housing 102 could be coupled to or include a proximate end 102a, a distal end 102b, and side ends having lips 102c, 102d, 102e and 102f. In one embodiment, housing 102 could be about 5 to 20 inches in length.

Proximate end 102a, distal end 102b, and side ends having elongated retaining lips 102c, 102d, 102e and 102f are collectively referred to herein as housing 102. It should be understood that housing 102 could be constructed of any suitable material such as a metallic material, plastic material, a polymer, or any suitable combination thereof and include any number of suitable labels, constructs, attachments, binding materials, and accessory-like elements. It should also be understood that housing 102 or parts of housing 102 may be constructed or assembled in any suitable manner including, for example, by tabs, screws, rivets, bolts, connectors, tight fits, tapes, adhesives, magnets, sleeves, other securing or retaining mechanisms, or any combination thereof.

In one embodiment, lips 102c, 102d, 102e and 102f aid in retaining active power cells 104a, 104b, 104c, and 104d (collectively, referred to herein as active power cells 104) in a particular fashion relative to each other and system 100. Active power cells 104 could include any suitably sized, shaped or configured frame, structure, frame-like structure, housing, housing-like structure, or any combination thereof according to one embodiment of the present disclosure. In one embodiment, active power cells 104 could include a first side exposed to the ambient environment and a second side exposed to the interior chamber of system 100.

In one embodiment, active power cells 104a and 104b shown in FIG. 1A could be included as a unitary structure or as two or more separate structures according to one embodiment of the present disclosure. Similarly, active power cells 104c and 104d shown in FIG. 1B could be included as a unitary structure or as two or more separate structures. In one embodiment, active power cells 104 could be about 5 to 20 inches in length. In one embodiment, active power cells 104a and 104b could be disposed adjacent to one another along median 106a as shown in FIGS. 1A and 1B. Likewise, active power cells 104c and 104 could be disposed adjacent to one another along median 106b. Medians 106a and 106b are collectively referred to herein as medians 106.

In one embodiment, each of active power cells 104 could include any suitable number, size, shape, or configuration of pass-through structures or apertures such as, for example, cell apertures 108a, 108b, 108c, and 108d as generally shown in FIGS. 1A and 1B. Cell apertures 108a, 108b, 108c and 108d (and any other cell apertures included in active power cells 104) are collectively referred to herein as cell apertures 108. Cell apertures 108 could include any suitably sized, shaped or configured structure to allow ambient airflow from the outside of system 100 to pass through to an internal area of system 100 and vice versa according to one embodiment of the present disclosure.

In one embodiment, cell apertures 108 could be arranged in multiple rows or in a somewhat honeycomb like structure according to one embodiment of the present disclosure. Each of cell apertures 108 could be disposed in a transverse fashion relative to housing 102 or medians 106, rather than disposed in a relatively parallel or perpendicular fashion relative to housing 102 or medians 106. As an example, each of cell apertures 108 could be transversely disposed about 45 degrees (plus or minus 20 degrees) relative to medians 106 according to one embodiment of the present disclosure.

In one exemplary embodiment, cell apertures 108a in active power cell 104a could be disposed about +45 degrees (plus or minus 20 degrees) relative to an x-axis of median 106a, while cell apertures 108b in active power cell 104b could be disposed about −45 degrees (plus or minus 20 degrees) relative to the same x-axis of median 104a.

In one exemplary embodiment, cell apertures 108c in active power cell 104c could be disposed about +45 degrees (plus or minus 20 degrees) relative to an x-axis of median 106b, while cell apertures 108d in active power cell 104d could be disposed about −45 degrees (plus or minus 20 degrees) relative to the same x-axis of median 106b.

In another embodiment, cell apertures 108 could be positioned between about plus or minus 20 degrees and 75 degrees relative to medians 106. In still other exemplary embodiments, the optimal disposition of cell apertures 108 could be about plus or minus 45 degrees relative to medians 106.

Active power cells 104, cell apertures 108, or any combination thereof could be uniformly or selectively coated or treated with one or more photocatalytic materials, such as titanium dioxide and similar compounds, according to one embodiment of the present disclosure. In one embodiment, active power cells 104 treated with such photocatalytic materials and energized by a centrally located UV light source, purifying the ambient air by converting toxic compounds to benign constituents. In one embodiment, active power cells 104, cell apertures 108, or any suitable combination thereof may be coated with a suitable hydrophilic photocatalytic coating having non-nano titanium dioxide with several transition elements added to the coating to enhance or optimize the overall photocatalytic effect.

Figure 2:
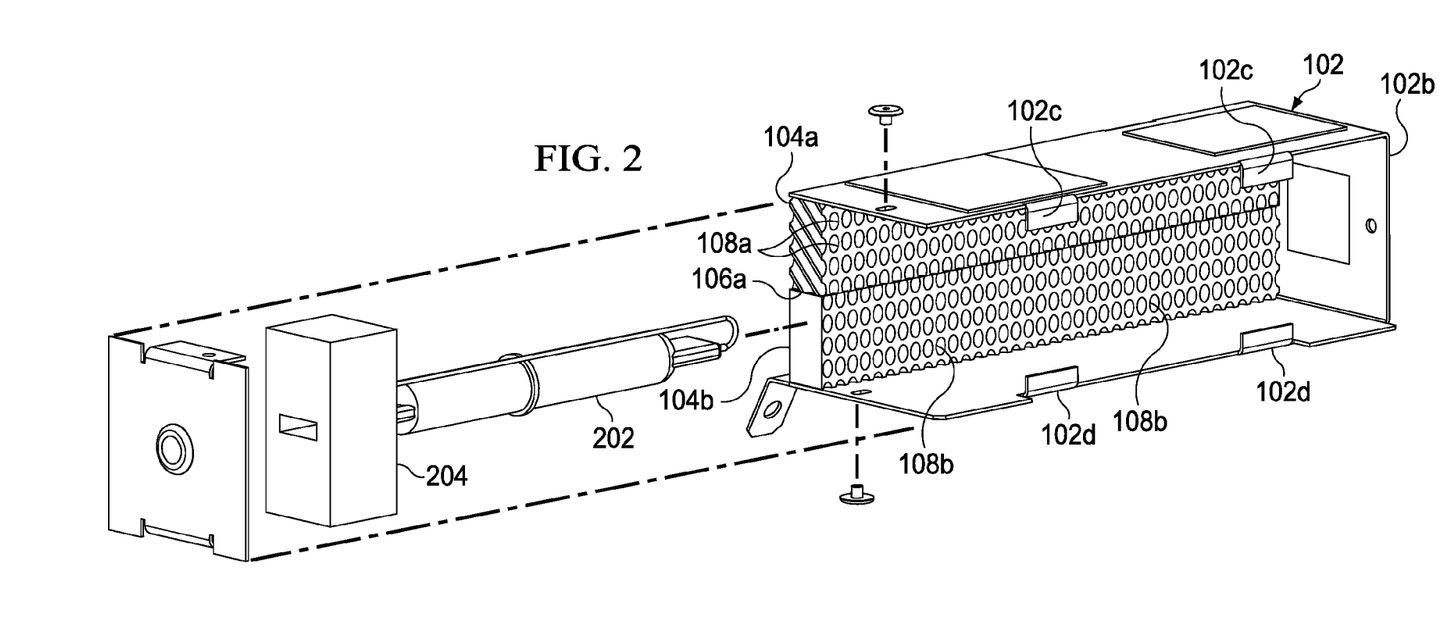
FIG. 2 is a somewhat simplified exploded view of the system shown in FIGS. 1A and 1B according to one embodiment of the present disclosure.

FIG. 2 is a somewhat simplified exploded view of assembly 200 of system 100 in accordance with one embodiment of the present disclosure. It should be understood that assembly 200 shown in FIG. 2 is for illustrative purposes only and that any other suitable view, system or subsystem could be used in conjunction with or in lieu of system 100 shown in assembly 200 according to one embodiment of the present disclosure.

In one embodiment, assembly 200 shown in FIG. 2 generally illustrates an unassembled system 100 shown in FIGS. 1A and 1B and could further include UV light source 202, spacer 204, and connector 206. As illustrated by FIGS. 1A and 2, when system 100 is fully assembled UV light source 202 is disposed between active power cells 104a, 104b, 104c, and 104d according to one embodiment of the present disclosure.

In one embodiment, UV light source 202 could include any suitably sized, shaped, or configured UV light source, UV lamp, UV bulb, other suitable sources of UV or UV subtype C (UVC) radiation, or any combination thereof providing a suitable amount of UV intensity according to one embodiment of the present disclosure. In one embodiment, UV light source 202 is of sufficient intensity to induce photocatalytic oxidation of active power cell 104. In still other embodiments, UV light source 202 includes, for example, a UV light source having a wavelength of 185 nanometers (nm) or 254 or a broad spectrum lamp capable of providing UV light having a wavelength of 185 nm and 254 nm, to induce photocatalytic oxidation of active power cell 104.

In one embodiment, when system 100 is assembled, spacer 204 aids in maintaining the relative position of UV light source 202 within housing 102. Although a particular configuration of spacer 204 is shown in FIG. 2, it should be understood that spacer 204 could include any suitable size, shape, or configuration according to one embodiment of the present disclosure. In one embodiment, spacer 204 could also be used to maintain the relative position of the lighting assembly 110 relative to housing 102 and connector 206 as generally shown in FIG. 2.

In one embodiment, connector 206 is part of lighting assembly 206 and is preferably electrically coupled with UV light source 202. Connector 206 could include any suitable connection to a power source (not shown) for lighting assembly 110 according to one embodiment of the present disclosure. Connector 206 could include any suitably sized, shaped, or configured connector including, for example, any suitable multiple pin connectors with two or more electrical contacts.

As illustrated by FIG. 2, when assembly 200 is fully assembled UV light source 202 is disposed between active power cells 104a, 104b, 104c, and 104d according to one embodiment of the present disclosure. Although active power cells 104 are disposed opposite from one another relative to UV light source 202, it should be understood that the relative positions and configurations of active power cells 104 could be varied in any suitable manner according to one embodiment of the present disclosure.

In one example, active power cells 104 could be disposed in three sides of housing 102 according to one embodiment. In one example, active power cells 104 could be disposed in a triangular manner encasing or substantially surrounding UV light source 202 according to one embodiment. In another example, active power cells 104 could be disposed in a box-like manner encasing or substantially surrounding opposing sides UV light source 202 according to another embodiment. As still another example, active power cells 104 could be disposed in a circular manner encasing or substantially surrounding UV light source 202 in still another embodiment.

FIGS. 3A, 3B, 3C and 3D are somewhat simplified partial cross sectional views 300a, 300b, 300c and 300d (collectively referred to herein as views 300) of exemplary active power cells 104 in accordance with embodiments of the present disclosure. It should be understood that views 300 shown in FIGS. 3A-3D are for illustrative purposes only and that any other suitable view, system or subsystem could be used in conjunction with or in lieu of active power cells 104 shown in views 300 according to one embodiment of the present disclosure.

Figure 3A:
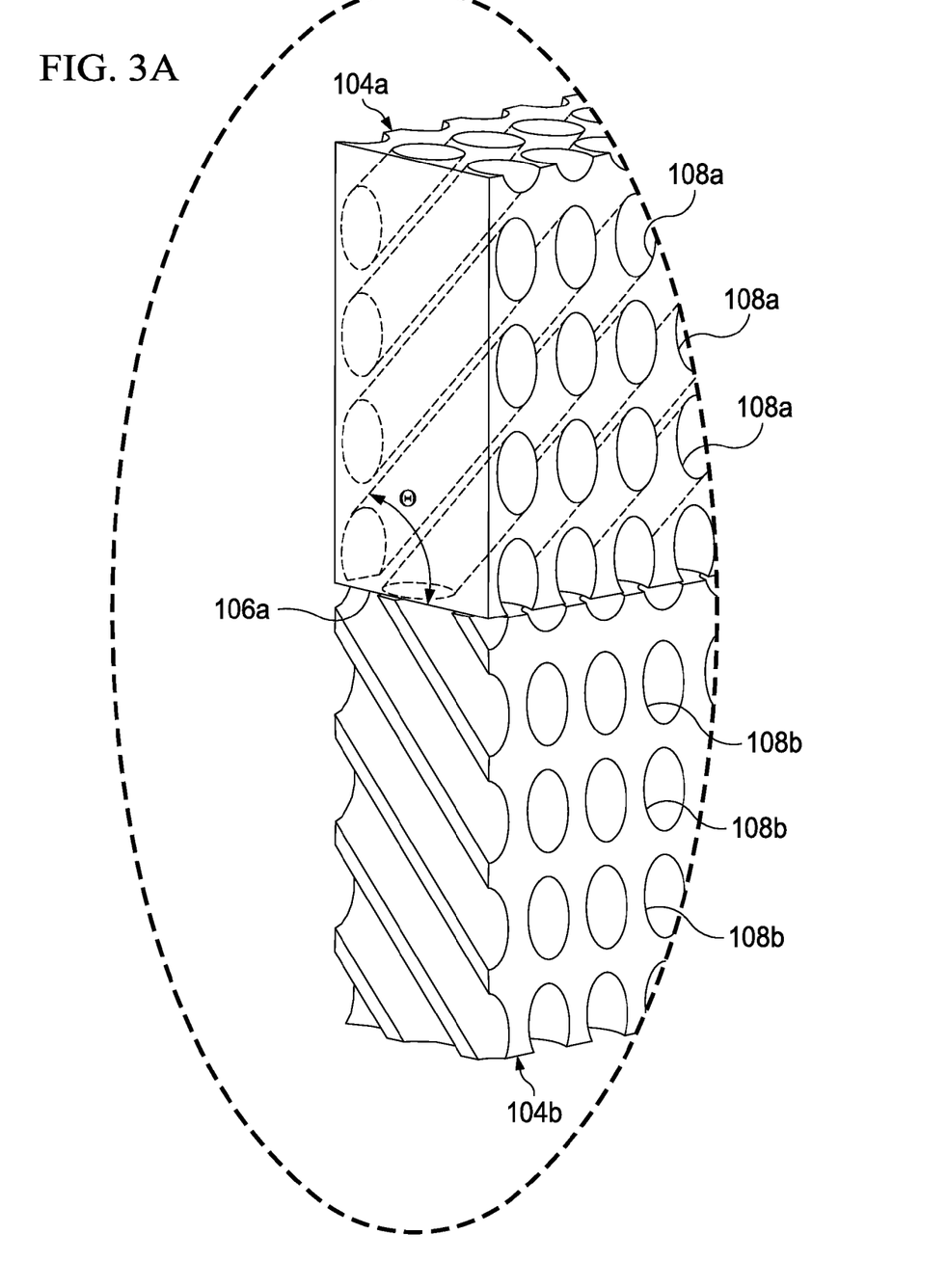
FIGS. 3A-D are a somewhat simplified partial cross sectional views of the system shown in FIGS. 1A, 1B and 2 according to one embodiment of the present disclosure.

In the embodiment shown in FIG. 3A, active power cells 104a and active power cells 104b are structurally independent from each other. Cell apertures 108a in active power cell 104a could be disposed in a transverse direction about minus θ degrees relative to an x-axis of median 106a, while cell apertures 108b in active power cell 104b could be disposed about positive θ degrees relative to the same x-axis of median 106a as shown in FIG. 3A. In an exemplary embodiment, active power cells 104a and active power cells 104b are structurally independent from each other. Cell apertures 108a in active power cell 104a could be disposed in a transverse direction about minus 45 degrees (plus or minus 20 degrees) relative to an x-axis of median 106a, while cell apertures 108b in active power cell 104b could be disposed about positive 45 degrees (plus or minus 20 degrees) relative to the same x-axis of median 106a as shown in FIG. 3A.

Figure 3B:
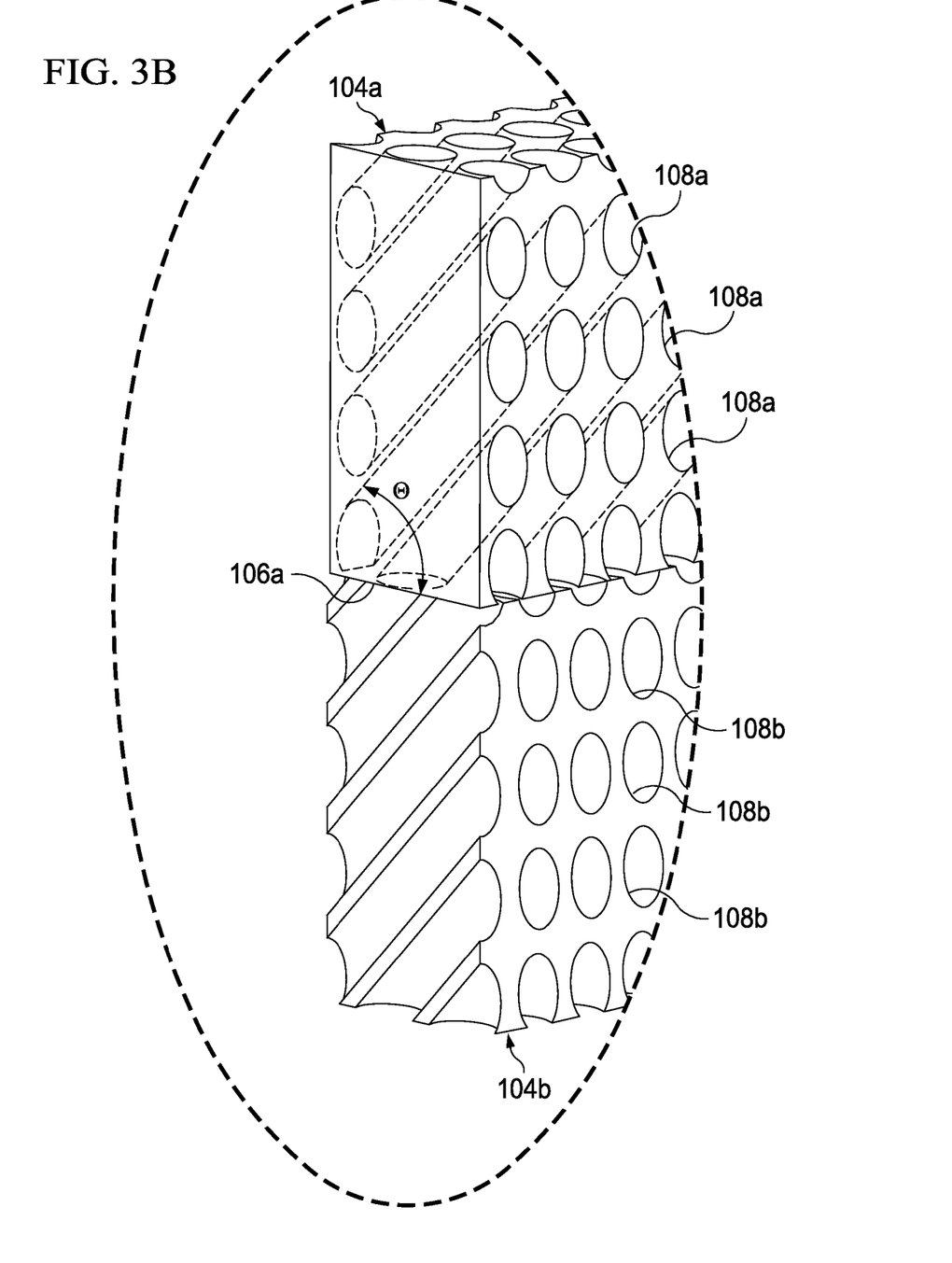

In the embodiment shown in FIG. 3B, active power cells 104a and active power cells 104b are two independent cells. Cell apertures 108a and 108b are disposed in the same transverse direction and are disposed about 45 degrees (plus or minus 20 degrees) relative to a reference axis found in active power cells 104.

Figure 3C:
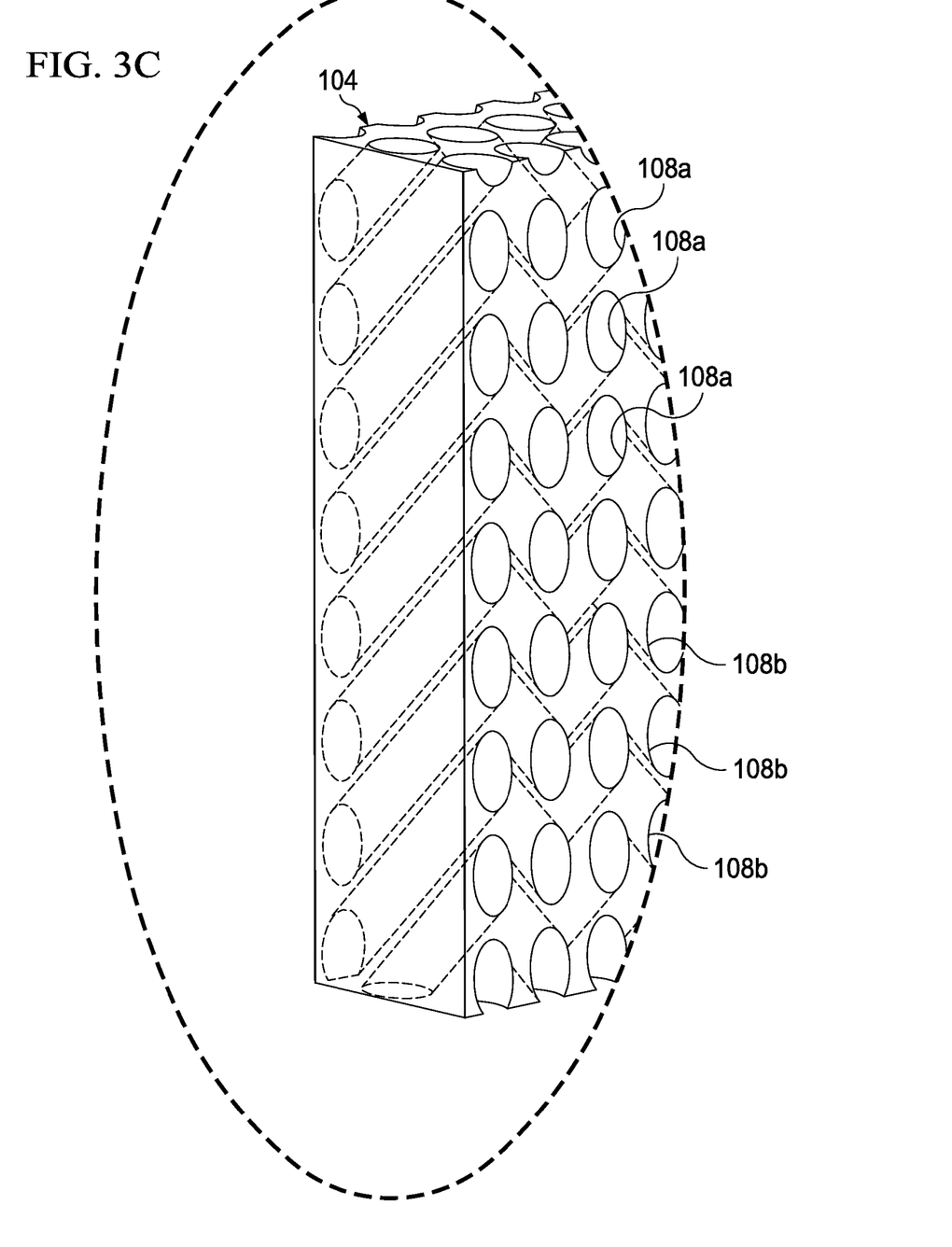

In the embodiment shown in FIG. 3C, active power cells 104a and active power cells 104b are included as a unitary structure. Cell apertures 108a in active power cell 104a are transversely disposed about minus 45 degrees (plus or minus 20 degrees) relative to an x-axis of median 106a, while cell apertures 108b are transversely disposed about positive 45 degrees (plus or minus 20 degrees) relative to a reference axis found in active power cells 104.

Figure 3D:
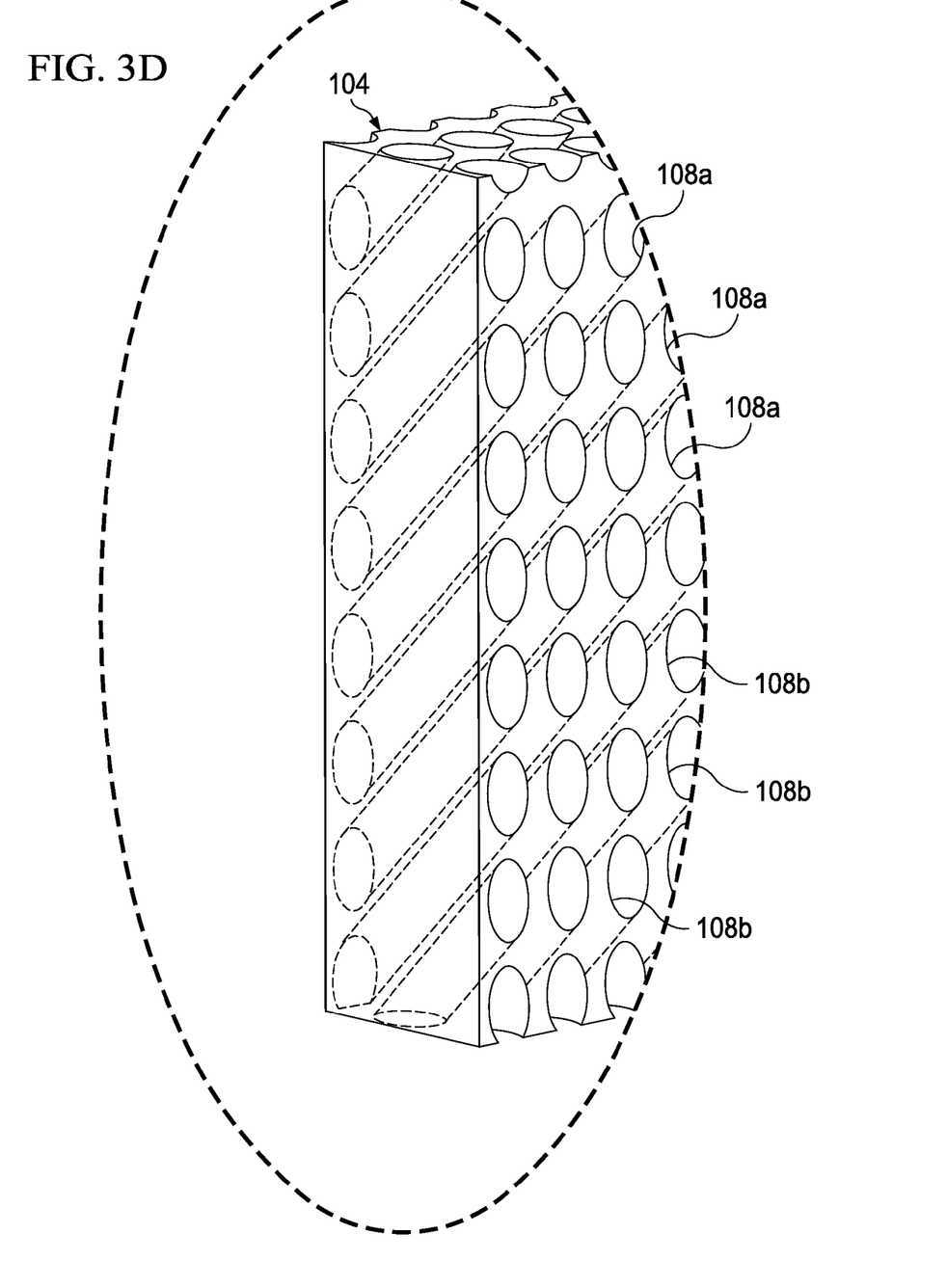

In the embodiment shown in FIG. 3D, active power cells 104a and active power cells 104b are included as a unitary structure. Cell apertures 108a and 108 are disposed in the same transverse direction and are disposed about 45 degrees (plus or minus 20 degrees) relative a reference axis found in active power cells 104.

In one embodiment of the present disclosure, the majority, if not all, of active power cells 104 in system 100 are capable of being energized by UV light source 204. By optimizing UV exposure to active power cells 104, system 100 maximizes the relative rates of photocatalytic oxidation, and thus rates of oxidation and purification of the ambient environment are greater than those of conventional oxidation systems, purification systems, or particle air purifiers and filters. In one embodiment, photocatalytic oxidation in system 100 could produce one or more of the following oxidizers: Hydroxyl Radicals (OH), Vaporized Hydrogen Peroxide ($H_2O_2$), Super Oxides ($O_2$—) or Low Level Ozone ($O_3$).

In one embodiment, active power cell 104 could include any suitably sized and dimensioned cell apertures 108 such as, for example, cell apertures 108 that are about 55 square millimeters ($mm^2$) in volume. In other embodiments, active power cell 104 could include cell apertures 108 where the average or median distance from an edge of one or more of call apertures 108 to the center of UV light source 202 having, for example, a diameter of about 20 mm, could be about 15 mm.

Figure 4:
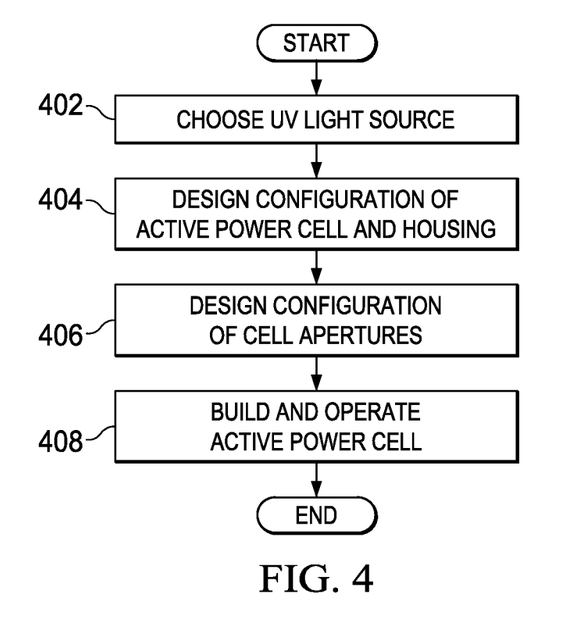
FIG. 4 is a somewhat simplified flow diagram generally illustrating a method of using the system shown in FIGS. 1A and 1B according to one embodiment of the present disclosure.

FIG. 4 is a somewhat simplified flow diagram generally illustrating method 400 of customizing and using active power cell 104 shown in FIGS. 1A, 1B, 2 and 3 in accordance with one embodiment of the present disclosure. Although a particular set of steps are illustrated as method 400, it should be understood that any number of steps may be included or removed in conjunction with the steps should as method 400 or in lieu of one or more steps of method 400 according to one embodiment of the present disclosure.

In one embodiment, method 400 could begin with step 402. Step 402 could include choosing a UV light source such as, for example, UV light source 202 shown in FIG. 2, of suitable size, shape and configuration for a particular photocatalytic oxidation and ambient environment oxidation and purification application.

In step 404, method 400 could include designing the configuration of active power cell and housing need to house the UV light source chosen in step 402. As examples, the active power cells could be designed to encase or substantially surround the chosen UV light source on opposing sides such as, for example, the relative positions of UV light source 202 and active power cells 104 shown in FIG. 2. In another design, the system could include designing a system where the active power cells are configured in a triangular fashion or circular fashion about the UV light source.

Depending on the active power cell configuration chosen, step 406 could include choosing the relative angle of the cell apertures in the active power cells. For example, step 406, cell apertures 108 shown in FIG. 3, could be configured to be about 45 degrees (plus or minus 20 degrees) from a reference point such as, for example, median 106 to maximize UV exposure to the respective surfaces of active power cell 104 and cell apertures 108.

Once design specifications in step 406 are complete, method 400 continues with step 408. Step 408 could include building and operating the active power cell to facilitate photocatalytic oxidation and air filtration. For example, by maximizing UV exposure to active power cells 104, the relative rates of photocatalytic oxidation with the ambient air and thus air filtration are maximized and are superior the same compared to conventional oxidation systems, purification systems, or particle air purifiers and filters.

Accordingly, embodiments of the present disclosure optimizing an active photocatalytic oxidation system to maximize potential ultraviolet (UV) light exposure to the surface and apertures of the active power cells, thus increasing the rates of photocatalytic oxidation and the oxidation and purification of the ambient environment.

It may be advantageous to set forth definitions of certain words and phrases used in the present disclosure. The terms "ambient" and "environment" and its respective derivatives refer to any surrounding areas, air, gasses, solids, liquids, organisms, or surfaces. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure and the following claims.

What is claimed is:

1. A photocatalytic oxidation system comprising:
   an elongate ultraviolet (UV) light source configured to emit UV light and having a UV source axis in the elongate direction;
   an active cell positioned proximate to the UV light source, the active cell comprising:
      a first side spaced from parallel to a second side;
      a plurality of apertures disposed in a first transverse manner from the first side to the second side, each aperture of a first set of apertures of the plurality of apertures having a first aperture surface, wherein the first transverse manner of the first set of apertures of the plurality of apertures comprises a relative disposition of about 20-70 degrees from a median axis along the first and second sides to thereby maximize an amount of UV light that impinges directly onto the first aperture surfaces radially from the UV source axis, which is parallel to the second side;
   wherein the second side and the first aperture surfaces are coated with a photocatalytic material configured to perform photocatalytic oxidation when exposed to UV light; and wherein the maximized amount of UV light impinging directly onto the first aperture surfaces maximizes a rate of photocatalytic oxidation.

2. The system of claim 1, wherein the active cell further comprises:
   a second set of apertures of the plurality of apertures, each aperture of the second set of apertures having a second aperture surface, the second set of apertures disposed in a second transverse manner from the first side to the second side to thereby maximize an amount of UV light that impinges directly onto the second aperture surfaces of the second set of apertures emitted radially from the elongate UV light source, wherein the second transverse manner of the second set of the apertures comprises a relative disposition of about negative 20-70 degrees from the median axis.

3. The system of claim 1, further comprising:
   a second active cell positioned proximate to the UV light source, the second active cell comprising:
      a first side spaced from an parallel to a second side;
      a second plurality of apertures disposed in a second transverse manner from the first side to the second side of the second active cell, each aperture of the second plurality of apertures having a second aperture surface, wherein the second transverse manner of the second plurality of apertures comprises a relative disposition of about 20-70 degrees from a second median axis along the first and second sides of the second active cell to thereby maximize an amount of UV light that impinges directly onto the second plurality of aperture surfaces emitted radially from the elongate UV light source;
   wherein the second side and the second plurality of aperture surfaces of the second active cell are coated with a photocatalytic material configured to perform photocatalytic oxidation when exposed to UV light; and wherein the UV light source is disposed between the first active cell and the second active cell; and wherein the maximized amount of UV light impinging directly onto the first aperture surfaces maximizes the rate of photocatalytic oxidation.

4. The system of claim 3 further comprising:
   a housing structure to maintain the disposition of UV source axis parallel with the first active cell's second side and the second active cell's second side.

5. An active photocatalytic oxidation system comprising:
   an elongate ultraviolet (UV) light source having a UV source axis in the elongate direction:
   a first active cell comprising:
      a first side exposed to an ambient environment;
      a second side exposed to the UV light source and parallel with the UV source axis;
      a first plurality of apertures disposed in a transverse manner from the first side to the second side wherein a first transverse manner of a first set of the first plurality of apertures comprises a relative disposition of about 20-70 degrees from a median axis along the first and second sides, each aperture of the first set of the first plurality of apertures has a first aperture surface comprising a photocatalytic material responsive to UV light from the UV light source, wherein the first transverse manner of the first set of the first plurality of apertures provide direct impingement of UV light emitted radially from the elongate UV light source onto a portion of all the first set of the first plurality of aperture surfaces.

6. The system of claim 5, wherein a second transverse manner of a second set of the first plurality of apertures also disposed from the first side to the second side comprises a relative disposition of about negative 20-70 degrees from the median axis, each aperture of the second set of apertures has a second aperture surface comprising a photocatalytic material responsive to UV light from the UV light source, and wherein the second transverse manner of the second set of the first plurality of apertures provide direct impingement of UV light emitted radially from the elongate UV light source onto a portion of all the second set of the first plurality of aperture surfaces.

7. The system of claim 5 wherein the first active cell is completely coated with a material capable of photocatalytic oxidation when exposed to ultraviolet (UV) light.

8. The system of claim 5 further comprising:
a second active cell, wherein the UV light source is disposed between the first active cell and the second active cell.

9. The system of claim 8, further comprising:
a housing structure to maintain the disposition of the UV light relative to the first active cell and the second active cell.

* * * * *